United States Patent

Kihara et al.

[11] Patent Number: 4,814,500
[45] Date of Patent: Mar. 21, 1989

[54] CYANOGUANIDINE DERIVATIVE AND PROCESS FOR PREPARATION THEREOF

[75] Inventors: Noriaki Kihara, Iwakuni; Teruaki Mukaiyama, Tokyo; Takeshi Ishitoku; Katsuya Takahashi, both of Ohtake, all of Japan

[73] Assignee: Mitsui Petrochemical Industries, Ltd., Tokyo, Japan

[21] Appl. No.: 91,850

[22] Filed: Sep. 1, 1987

[30] Foreign Application Priority Data

Sep. 1, 1986 [JP] Japan .................................. 61-203640

[51] Int. Cl.⁴ .......................................... C07C 129/08
[52] U.S. Cl. ..................................... 564/104; 548/342
[58] Field of Search ........................................ 564/104

[56] References Cited

U.S. PATENT DOCUMENTS 3,950,333  4/1976  Durant et al. ...................... 544/244

FOREIGN PATENT DOCUMENTS 0092257  5/1985  Japan .................................. 564/104
0105661  6/1985  Japan .................................. 564/104

OTHER PUBLICATIONS

Caldero, G. et al, "N–Cyano–N'–Methyl–2–[(-5–Methyl, etc.]", C.A. 89, 146904g, Oct. 1978.

Primary Examiner—Glennon H. Hollrah
Assistant Examiner—S. Treanor
Attorney, Agent, or Firm—Sherman and Shalloway

[57] ABSTRACT

A novel cyanoguanidine derivative represented by the following general formula (I):

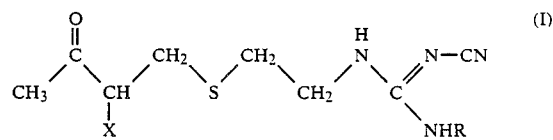

wherein X stands for a hydrogen atom, a chlorine atom or a bromine atom, and R stands for a lower alkyl group, is an effective precursor for the synthesis of N-cyano-N'-methyl-N''-(2-(5-methyl-4-imidazolylmethylthio(ethyl)-guanidine (Cimetidine) which has an action of controlling secretion of gastric acid and is valuable as an agent for the remedy of a gastric ulcer.

This cyanoguanidine derivative is prepared by reacting a methylvinylketone derivative with a mercaptoguanidine derivative or by reacting an amidinoketone derivative with a halogenating agent.

1 Claim, No Drawings

CYANOGUANIDINE DERIVATIVE AND PROCESS FOR PREPARATION THEREOF

BACKGROUND OF THE INVENTION

(1) Field of the Invention

The present invention relates to a novel cyanoguanidine derivative which is a precursor for the synthesis of N-cyano-N'-methyl-N"-(2-(5-methyl-4-imidazolylmethylthio)ethyl)guanidine (Cimetidine; often referred to as "Cimetidine" hereinafter), which has an action of controlling secretion of gastric acid and is valuable as an agent for the remedy of a gastric ulcer, and a process for the preparation of this cyanoguanidine derivative.

(2) Description of the Prior Art

Imidazole derivatives such as 4-hydroxymethyl-5-methylimidazole disclosed in Japanese patent application laid-open specification No. 142271/81, 4-(2-aminoethylthio)-5-methylimidazol disclosed in Japanese patent application laid-open specification No. 42661/72 and ((4-methyl-5-imidazolyl)methylthioethyl)-S-methylisothiourea disclosed in Japanese patent application laid-open specification No. 7557/74 are mainly used as the precursor for the synthesis of Cimetidine, and Cimetidine can be derived from these imidazole derivatives. Separately, N-cyano-N'-2-2(2,3-diketobutylthio)ethyl-N"-methylguanidine disclosed in Spanish Pat. No. 455,991 (Chemical Abstracts, 89, 146904I (1978)) can be mentioned as the precursor that can be converted to Cimetidine by forming an imidazole ring at the final step. A diacetyl compound which is a starting compound for the synthesis of this precursor has a violent foul smell and aggravates the working environment, and the yield of the precursor is not sufficiently high.

SUMMARY OF THE INVENTION

We made research with a view to developing a reasonable process for the synthesis of Cimetidine from starting materials not including a smell-generating substance by a reduced number of steps in a good working environment, and we found a novel cyanoguanidine derivative quite different from the derivatives disclosed in the above-mentioned prior art references and we clarified that Cimetidine can be synthesized at a high efficiency if this novel derivative is used as the precursor. We have now completed the present invention based on this finding.

More specifically, in accordance with the present invention, there is provided a novel cyanoguanidine derivative as a precursor for the synthesis of Cimetidine valuable as an agent for the remedy of a gastric ulcer, which derivative is represented by the following general formula (I):

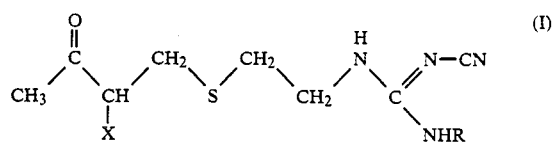

wherein X stands for a hydrogen atom, a chlorine atom or a bromine atom, and R stands for a lower alkyl group.

Furthermore, in accordance with the present invention, there is provided a process for the preparation of this novel cyanoguanidine derivative, which comprises reacting a methylvinylketone derivative represented by the following general formula (II):

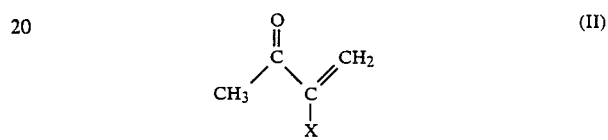

wherein X stands for a hydrogen atom, a chlorine atom or a bromine atom, with a mercaptoguanidine derivative represented by the following general formula (III):

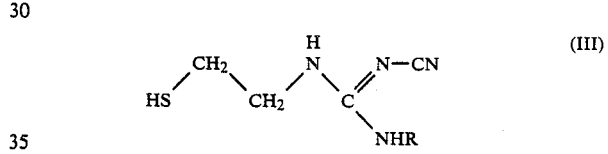

wherein R stands for a lower alkyl group, or reacting a guanidinoketone derivative represented by the following general formula (I-2):

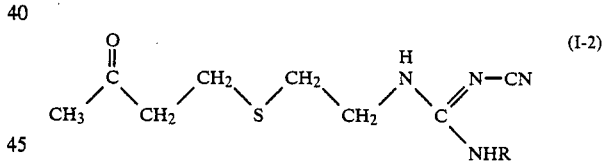

wherein R stands for a lower alkyl group, with a halogenating agent.

DETAILED DESCRIPTION OF THE PREFERRED EMBODIMENT

The cyanoguanidine derivative of the general formula (I) according to the present invention can be synthesized by the process represented by the following reaction formulae.

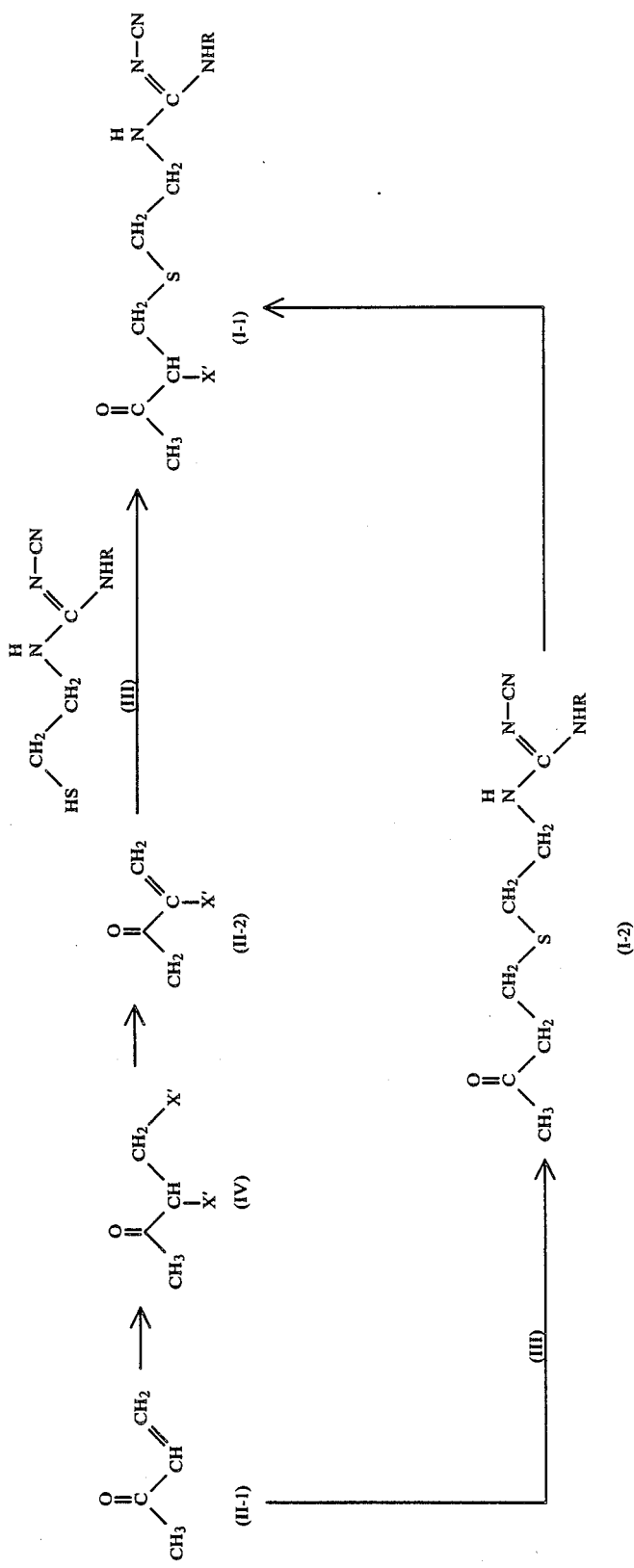

In the above reaction formulae, X stands for a chlorine atom or bromine atom, and R is as defined above.

The compound (IV) is easily obtained by reacting methylvinylketone (II-1), which is easily available and can be easily handled, with chlorine or bromine according to known procedures, and the compound (II-2) can be easily obtained by dehydrohalogenating the compound (IV) in the presence of a base. The intended cyanoguanidine derivative (I-1) can be obtained substantially quantitatively by adding a known compound of the formula (III) to the so-obtained compound (II-2). The present invention is advantageous in that the Cimetidine precursor (I-1) can be derived from the compound (II-1) according to the so-called one-pot reaction without isolation of any of the intermediates. The compound (I-2) in which X in the general formula (I) is a hydrogen atom can be quantitatively obtained by reacting the compound (II-1) with a known compound of the formula (III). Furthermore, the compound (I-1) can be derived from the compound (I-2) by reacting it with a halogenating agent such as chlorine or bromine.

The novel cyanoguanidine derivative of the present invention is represented by the general formula (I-1) or (I-2) or collectively by the general formula (I). In each formula, X stands for a hydrogen atom, a chlorine atom or a bromine atom, and R stands for a lower alkyl group such as a methyl group, an ethyl group or an n-propyl group.

Examples of the novel cyanoguanidine derivative of the present invention are shown below.

$$CH_3-\overset{O}{\underset{\|}{C}}-\overset{}{\underset{X}{CH}}-CH_2-S-CH_2-CH_2-\overset{H}{\underset{}{N}}-\overset{N-CN}{\underset{NHR}{C}}$$

| Compound No. | X  | R   |
|--------------|----|-----|
| 1            | H  | Me  |
| 2            | Cl | Me  |
| 3            | Br | Me  |
| 4            | H  | Et  |
| 5            | Cl | Et  |
| 6            | H  | Pr$^n$ |

The novel cyanoguanidine derivative represented by the general formula (I) is synthesized according to the above-mentioned reaction formulae.

The cyanoguanidine derivative in which X in the general formula (I) is a chlorine atom or a bromine atom, that is, the compound (I-1), can be substantially quantitatively obtained by deriving the compound (II-2) from methylvinylketone (II-1) according to a known process, for example, a process disclosed in Helv. Chim. Acta, 62, page 442 (1979) or Azerbaidzhanskii Khimicheskii Zhurnal, No. 5, page 59 (1975) and reacting the compound (II-2) with the known compound (III). In this case, the compound (III) is ordinarily used in a substantially equimolar amount to the compound (II-2). An organic solvent such as methylene chloride, chloroform, methanol, ethanol, methyl acetate or ethyl acetate is used as the reaction solvent, and methanol and ethanol are preferred. The reaction temperature is −20° to 50° C., preferably −10° to 10° C. In order to perform the preparation of the intended compound (I-1) from methylvinylketone (II-1) by one-pot reaction, it is preferred that the respective reactants be used in equivalent amounts, and a halogenated hydrocarbon such as chloroform or methylene chloride is preferably used as the solvent. At each step, the reaction can be carried out at a temperature of −20° to 40° C., preferably −10° to 10° C.

The novel cyanoguanidine derivative in which X in the general formula (I) is a hydrogen atom, that is, the compound of the formula (I-2), can be quantitatively obtained by reacting the vinylketone (II-1) with the known compound (III). It is preferred that the known compound (III) be used in a substantially equimolar amount to methylvinylketone (II-1). An organic solvent such as methylene chloride, chloroform, methanol, ethanol, methyl acetate or ethyl acetate can be used as the reaction solvent, and methanol and ethanol are preferred. The reaction temperature is −30° to 50° C., preferably 0° to 30° C., and the reaction time is 0.5 to 5 hours, preferably 1 to 2 hours. Conversion of the compound (I-2) to the compound (I-1) can be accomplished by using a halogenating agent in an amount of 1 to 2 equivalents to the compound (I-2). As the halogenating agent, there can be used, for example, chlorine, bromine and N-bromosuccinimide. An organic solvent such as acetic acid, chloroform and methylene chloride can be used as the reaction solvent, and acetic acid is especially preferred. The reaction temperature is 5° to 50° C., preferably 5° to 20° C., and the reaction time is 0.5 to 5.0 hours, preferably 1 to 2 hours.

After the reaction, the intended compound can be isolated only by removing the solvent from the reaction mixture, and the recovered intended compound has a sufficiently high purity. If a product having a higher purity is desired, the recovered product is subjected to the column chromatography.

Examples of synthesizing Cimetidine from the compound of the present invention represented by the general formula (I-1) will now be described.

(1) A process which comprises reacting the above-mentioned cyanoguanidine derivative with an ammonium salt of an organic acid and a formic acid derivative (see Japanese patent application No. 203642/86).

This process is preferred because the reaction yield is high. As the ammonium salt of the organic acid (RCONH$_4$), there can be mentioned ammonium salts of aliphatic carboxylic acids such as ammonium formate, ammonium acetate and ammonium propionate, and ammonium salts of aromatic carboxylic acids such as ammonium benzoate, ammonium p-toluate and ammonium naphtoate. As the formic acid derivative (HC(OR')$_3$HCOOR") used for the above reaction, there can be mentioned ortho-formic acid esters such as methyl ortho-formate and ethyl ortho-formate, and formic acid esters such as methyl formate, ethyl formate, propyl formate and phenyl formate. The reaction can be carried out in an organic solvent or in the absence of a solvent. As the reaction solvent, the can be mentioned, for example, aliphatic alcohols such as methanol, ethanol, propanol and isopropanol, aromatic hydrocarbons such as benzene, toluene and xylene, ethers such as diethyl ether, tetrahydrofuran and dioxane, nitriles such as acetonitrile and propionitrile, halogenated hydrocarbons such as dichloromethane, chloroform, carbon tetrachloride and dichloroethane, aliphatic carboxylic acids such as formic acid and acetic acid, heterocyclic aromatic compounds such as pyridine and picolinen, and amides such as formamide and dimethylformamide.

The ammonium salt of the organic acid is used in an amount of 1 to 50 moles, preferably 2 to 10 moles, per mole of the cyanoguanidine derivative, and the formic acid derivative is used in an amount of 1 to 50 moles, preferably 2 to 10 moles, per mole of the cyanoguanidine derivative. The amount of the solvent is 2 to 50 times (by weight), preferably 5 to 30 times (by weight), the amount of the cyanoguanidine derivative. The reaction temperature is 20° to 200° C., preferably 60° to 150° C., and the reaction time is 10 minutes to 5 hours, preferably 30 minutes to 3 hours. After the reaction, separation and purification can be performed according to customary procedures to obtain Cimetidine.

(2) A process which comprises reacting the above-mentioned cyanoguanidine derivative with formamidine formate represented by the following formula (see Japanese patent application No. 24482/87):

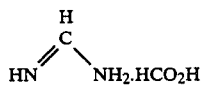

According to this process, a reaction yield much higher than the yield attained in the above-mentioned process (1) can be attained, and formamidine formate is cheap. Moreover, formylation of the cyanoguanidine derivative to an α-acyloxyketone derivative represented by the following formula:

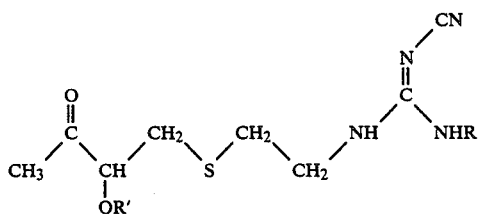

wherein R' stands for

is advanced in a high yield, and an imidazole ring can be subsequently used. Since it is considered that formamidine formate acts as a dehydrating agent, Cimetidine and a related compound of Cimetidine can be obtained continuously in one reaction vessel, that is, economically advantageously. Therefore, this process is excellent.

Formamidine formate may be used in the form of a reaction mixture obtained by reaction a formic acid derivative such as methyl ortho-formate or ethyl ortho-formate with ammonium formate or by reacting ammonia with the above-mentioned ortho-formic acid ester in the presence of a formic acid salt as the solvent, or formamidine formate may be used after isolation from this reaction mixture.

An example of the production of formamidine formate will be described in Referential Example 3 given hereinafter.

This reaction can be carried out in the absence of a solvent, but preferably, the reaction is carried out in an organic solvent. As the organic solvent, there can be mentioned aliphatic alcohols such as methanol, ethanol, propanol, isopropanol and methyl cellosolve, aromatic hydrocarbons such as benzene, toluene and xylene, ethers such as diethyl ether, tetrahydrofuran and dioxane, nitriles such as acetonitrile and propionitrile, halogenated hydrocarbons such as dichloromethane, chloroform, carbon tetrachloride and dichloroethane, aliphatic carboxylic acids such as formic acid and acetic acid, heterocyclic aromatic compounds such as pyridine and picoline, and amides such as formamide, dimethylformamide and N-methylpyrrolidone. Formamide, dimethylformamide, isopropanol and methyl cellosolve are preferred.

The solvent is used in an amount 2 to 50 times (by weight), preferably 5 to 30 times (by weight), the amount of the cyanoguanidine derivative. Formamidine formate is used in an amount of 1 to 50 moles, preferably 2 to 20 moles, per mole of the cyanoguanidine derivative. The reaction temperature is 0° to 70° C., preferably 5° to 30° C., and the reaction time is 10 minutes to 5 hours, preferably 30 minutes to 3 hours. The α-acyloxyketone derivative is formed by this operation, but the so-formed derivative is further reacted, without isolation, at an elevated temperature of 20° to 200° C., preferably 60° to 150° C., for 10 minutes to 5 hours, preferably 30 minutes to 3 hours. Any particular catalyst need not be used for this reaction of the latter stage, but it is preferred that the reaction be carried out in the presence of an inorganic phosphoric acid salt. As the inorganic phosphoric acid salt, there can be mentioned, for example, anhydrides and hydrates of hypophosphorous acid salts such as sodium hypophosphite and potassium hypophosphite, phosphorous acid salts such as sodium monohydrogenphosphite and potassium monohydrogenphosphite, hypophosphoric acid salts such as sodium monohydrogenhypophosphate and sodium dihydrogenhypophosphate, metaphosphoric acid salts such as sodium metaphosphate and potassium metaphosphate, polyphosphoric acid salts such as sodium pyrophosphate and sodium tripolyphosphate, and ortho-phosphoric acid salts such as sodium ammonium hydrogenphosphate and sodium diammonium phosphate. Anhydrides and hydrates of ortho-phosphoric acid salts such as sodium ammonium hydrogenphosphate, lithium ammonium hydrogenphosphate, potassium ammonium hydrogenphosphate and sodium dihydrogenphosphate are preferred. These salts may be used in the form of mixtures of two or more of them.

The inorganic phosphoric acid salt is used in an amount of 0.1 to 10 moles, preferably 1 to 5 moles, per mole of the cyanoguanidine derivative.

Instead of the above-mentioned two-staged method, there may be adopted a method in which the above-mentioned amounts of the reactants and solvent are charged and the reaction is carried out at a temperature of 20° to 200° C., preferably 60° to 150° C., for 10 minutes to 5 hours, preferably 30 minutes to 3 hours, whereby Cimetidine is obtained. Any catalyst need not be particularly used, but it is preferred that the reaction be carried out in the presence of an inorganic phosphoric acid salt.

Ordinary separating and purifying means such as column chromatography and recrystallization can be adopted, after the reaction, for obtaining intended Cimetidine or an analogous compound thereof.

In addition to the foregoing processes, there may be adopted the following processes, though the detailed description is omitted.

(3) A process which comprises reacting the cyanoguanidine derivative with formamidine in the presence of ammonia (see Japanese patent application No. 203643/86).

(4) A process which comprises reacting the cyanoguanidine derivative with an imidate represented by the following formula:

$$HN=C\begin{matrix}H\\\\OR^2\end{matrix}$$

wherein $R^2$ stands for a lower alkyl group, an aryl group or an aroyl group, and an ammonium salt or liquid ammonia (see Japanese patent application No. 203641/86).

(5) A process which comprises reacting the cyanoguanidine derivative with an aminoacetal derivative represented by the following general formula:

$$HC\begin{matrix}OR^2\\\\OR^3\\|\\NR^4R^5\end{matrix}$$

wherein $R^2$, $R^3$, $R^4$ and $R^5$, which may be the same or different, stand for an alkyl group, in the presence of an ammonium salt of an organic acid of the formula $R^6COOHNH_3$ in which $R^6$ stands for a hydrogen atom or an alkyl group (see Japanese patent application No. 223782/86).

(6) A process which comprises reacting the cyanoguanidine derivative with an ammonium salt of a carboxylic acid and formic acid derivative (Japanese patent application No. 269728/86).

The present invention will now be described in detail with reference to the following examples.

EXAMPLE 1

This example illustrates the preparation of N-cyano-N'-methyl-N''-(2-(2-chloro-3-oxobutylthio)ethyl)guanidine (compound No. 2).

A 100-ml two-necked flask was charged with 4.7 g of 3-chloro-3-buten-2-one and 40 ml of ethanol, and a solution of 4.7 g of N-cyano-N'-methyl-N''-(2-mercaptoethyl)guanidine in 20 ml of ethanol was gradually added dropwise with stirring at $-5°$ C. After the dropwise addition, the mixture was stirred for 1 hour while maintaining the temperature below 0° C. Ethanol was removed by distillation under reduced pressure to obtain 7.4 g of a light brown liquid (the yield was 95%).

Thin layer chromatography: Rf 0.68 (Merck Co., alumina type E, ethyl acetate, 25° C.).

Mass spectrum: 226 (M+-HCl).

IR spectrum (liquid, cm$^{-1}$): 3420, 3290, 3015, 2160, 1720, 1580.

$^1$H-NMR spectrum (CDCl$_3$ solution, ppm):

$$CH_3\underset{(a)}{-}\overset{O}{\underset{\|}{C}}-\underset{\underset{Cl}{|}}{CH}\underset{(d)}{-}CH_2\underset{(b)}{-}S-CH_2\underset{(e)}{-}CH_2-\underset{\underset{H}{|}}{N}\underset{(g)}{-}C\begin{matrix}\diagup NCN\\\\\diagdown N-CH_3\\H\quad(c)\\(g)\end{matrix}$$

(a) 2.39 (3H, s)
(b) 2.78 (2H, m)
(c) 2.90 (3H, d, J=5.4 Hz)
(d) 3.06 (2H, m)
(e) 3.48 (2H, m)
(f) 4.40 (1H, dd, J=6.3 and 8.1 Hz)
(g) 6.60–7.20 (2H, m)

EXAMPLE 2

This example illustrates the preparation of N-cyano-N'-methyl-N''-(2-(2-chloro-3-oxobutylthio)ethyl)guanidine (compound No. 2).

A 300-ml two-necked flask equipped with a dropping funnel and a thermometer was charged with 13.3 g of 3,4-dichloro-2-butanone and 100 ml of ethanol, and a solution of 9.6 g of triethylamine in 10 ml of ethanol was added dropwise over a period of 15 minutes with stirring at a temperature maintained below 0° C. After the dropwise addition, the mixture was stirred for 30 minutes at the above temperature. Then, a solution of 10.0 g of N-cyano-N'-methyl-N''-(2-mercaptoethyl)guanidien in 30 ml of ethanol was gradually added dropwise to the mixture, and then, the mixture was stirred at room temperature for 1 hour. Ethanol was removed by distillation under reduced pressure, and water was added to the residue and the mixture was extracted with ethyl acetate, washed with a saturated aqueous solution of sodium chloride and dried on anhydrous magnesium sulfate. Ethyl acetate was removed by distillation under reduced pressure to obtain 16.1 g of the intended compound in the form of a brown liquid (the yield was 97%).

EXAMPLE 3

This example illustrates the preparation of N-cyano-N'-methyl-N''-(2-(2-bromo-3-oxobutylthio)ethyl)guanidine (compound No. 3).

A solution of 2.30 g (10 millimoles) of 3,4-dibromo-2-butanone in 20 ml of ethanol was cooled to $-25°$ C., and a mixture comprising 1.01 g (10 millimoles) of triethylamine and 5 ml of ethanol was added dropwise to the solution with stirring over a period of 5 minutes. Subsequently, the mixture was stirred at the above temperature for 30 minutes. Then, a solution of 1.58 g (10 millimoles) of N-cyano-N'-methyl-N''-(2-mercaptoethyl)guanidine in 5 ml of ethanol was added dropwise to the mixture over a period of 10 minutes. After the dropwise addition, the temperature was elevated to room temperature and reaction was further carried out for 1 hour at room temperature. The solvent was removed by distillation under reduced pressure at a temperature below 30° C. The obtained residue was separated and purified by the neutral alumina column chromatography (developing solvent: ethyl acetate) to obtain 0.68 g of the intended compound in the form of a colorless oily substance (the yield was 22%).

Thin layer chromatography: Rf 0.60 (alumina glass plate, Merck, Type E, developing solvent=ethyl acetate).

$^1$H-NMR spectrum (CDCl$_3$ solution; ppm):

(a) 2.40 (3H, s)
(b) 2.79 (2H, m)
(c) 2.93 (3H, d, J=5 Hz)
(d) 3.07 (2H, m)
(e) 3.48 (2H, m)
(f) 4.61 (1H, dd, J=6.9 Hz)
(g), (h) 6.3–6.8 (2H, m)

Infrared absorption spectrum (NaCl; cm$^{-1}$): 3290, 3015, 2160, 1715, 1580.

EXAMPLE 4

This example illustrates the preparation of N-cyano-N'-methyl-N''-(2-(3-oxobutylthio)ethyl)guanidine (compound No. 1).

A solution of 4.9 g (31 millimoles) of N-cyano-N'-methyl-N''-(2-mercaptoethyl)guanidine in 50 ml of ethanol was stirred at room temperature, and a mixture comprising 3.25 g (45 millimoles) of methylvinylketone and 10 ml of ethanol was added dropwise to the solution over a period of 10 minutes. The mixture was further stirred at room temperature for 2 hours. After the reaction, the solvent was removed by distillation under reduced pressure, and the residue was separated and purified by the silica gel column chromatography (developing solvent: methylene chloride/methanol=20/1) to obtain 6.8 g of the intended compound in the form of a colorless crystal (the yield was 96%).

Melting point: 48° to 51° C.

$^1$H-NMR spectrum (CDCl$_3$; ppm):

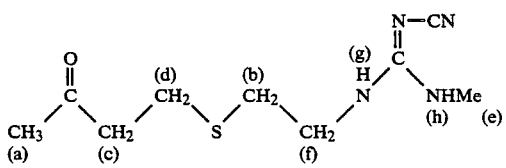

(a) 2.20 (3H, s)
(b) 2.72 (2H, t, J=7 Hz)
(c), (d) 2.79 (4H, s)
(e) 2.90 (3H, d, J=5 Hz)
(f) 3.49 (2H, q, J=7 Hz)
(g) or (h) 5.72 (1H, bs)
(h) or (g) 5.95 (1H, bs)

Infrared absorption spectrum (KBr; cm$^{-1}$): 3360, 2160, 1708, 1602, 1577.

REFERENTIAL EXAMPLE 1

This example illustrates the preparation of 3-chloro-3-buten-2-one.

A 100-ml two-necked flask equipped with a dropping funnel and a thermometer was charged with 6.3 g of 3,4-dichloro-2-butanone (prepared according to the process disclosed in Helv. Chim. Acta, 62, page 442 (1979)) and 40 ml of chloroform, and while maintaining the reaction temperature at −5° C., 5.0 g of triethylamine was gradually added. The mixture was stirred at −5° C. for 30 minutes, washed with water and dried on anhydrous magnesium sulfate. Chloroform was removed by distillation under reduced pressure while maintaining the water bath temperature below 35° C., whereby 4.0 g of the intended compound was obtained in the form of a light-yellow liquid (the yield was 86%).

$^1$H-NMR spectrum (CDCl$_3$; ppm):

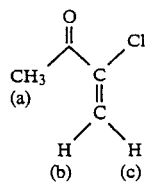

(a) 2.50 (3H, s)
(b) 6.49 (1H, d, J=2.7 Hz)
(c) 6.20 (1H, d, J=2.7 Hz)

REFERENTIAL EXAMPLE 2

This example illustrates the synthesis of 2-bromo-1-buten-3-one.

A solution of 1.15 g (5 millimoles) of 3,4-dibromo-2-butanone in 20 ml of chloroform was cooled to −20° C., and 0.5 g (5 millimoles) of triethylamine was added dropwise to the solution with stirring and the temperature was gradually elevated to room temperature. The reaction mixture was washed with a saturated aqueous solution of sodium chloride to which ice was added. The oil layer was dried by sodium sulfate, and the solvent was removed by distillation under reduced pressure to obtain 0.63 g of the intended compound in the form of a colorless oil (the yield was 85%).

$^1$H-NMR spectrum (CDCl$_3$; ppm):

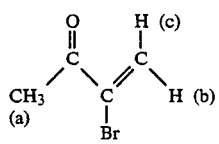

(a) 2.50 (3H, s)
(b) 6.53 (1H, d, J=3 Hz)
(c) 6.92 (1H, d, J=3 Hz)

EXAMPLE 5

This example illustrates the preparation of N-cyano-N'-methyl-N''-(2-(2-bromo-3-oxobutylthio)ethyl)guanidine (compound No. 3).

To a mixture comprising 0.57 g (2.5 millimoles) of N-cyano-N'-methyl-N''-(2-(3-oxobutylthio)ethyl)guanidine (compound No. 1) and 5 ml of acetic acid was added 0.81 g (2.5 millimoles) of a 25% solution of hydrogen bromide in acetic acid, and the mixture was cooled to 5° C. A solution of 0.4 g (2.5 millimoles) of bromine in 1 ml of acetic acid was added dropwise to the mixture with stirring, and the temperature was gradually elevated to room temperature and the mixture was further stirred at this temperature for 1 hour. After the reaction, the solvent was removed by distillation under reduced pressure. The residue was analyzed by the $^1$H-NMR spectrum and the alumina thin layer chromatography (Merck Co., Type E), and it was confirmed that the same substance as the intended compound synthesized in Example 3 was formed.

EXAMPLE 6

This example illustrates the preparation of N-cyano-N'-methyl-N''-(2-(2-chloro-3-oxobutylthio)ethyl)guanidine (compound No. 2) by the one-pot reaction.

A 100-ml three-necked flask equipped with a dropping funnel and a thermometer was charged with 1.33 g of methylvinylketone and 20 ml of chloroform, and the mixture was bubbled with 1.1 equivalents of chlorine gas at −5° C. with stirring and the mixture was stirred in this state for 20 minutes. Then, the mixture was bubbled with nitrogen gas to expel the excess of chlorine gas. While maintaining the temperature at −5° C., 2.1 g of triethylamine was gradually added dropwise to the mixture, and after the dropwise addition, the mixture was stirred for 30 minutes and a solution of 2.0 g of N-cyano-N'-methyl-N"-(2-mercaptoethyl)guanidine in 4.0 ml of chloroform was added dropwise to the mixture. The mixture was further stirred at room temperature for 1 hour. Chloroform was removed by distillation under reduced pressure, and precipitated triethylamine hydrochloride was dissolved in water and extracted with ethyl acetate. The ethyl acetate layer was dried by anhydrous magnesium sulfate and ethyl acetate was removed by distillation under reduced pressure to obtain 3.0 g of the intended compound in the form of a brown liquid (the yield was 91%). From the IR spectrum and NMR spectrum, it was confirmed that the obtained compound was the same as the product obtained in Example 1.

REFERENTIAL EXAMPLE 3

This example illustrates the preparation of formamidine formate.

A 100-ml reaction vessel was charged with 6.3 g (0.1 mole) of ammonium formate and 23.5 g (0.2 mole) of methyl ortho-formate, and the mixture was heated at 100° C. Since methanol and methyl formate were formed as the reaction was initiated and advanced, they were removed by a Dean-Stalk apparatus. Three hours were necessary for completion of the reaction. After the reaction, the reaction solution was placed under reduced pressure for 30 minutes by a vacuum pump, and 50 ml of dioxane was added to the residue and the mixture was stirred to precipitate a solid. The solid was recovered by filtration and washed with 10 ml of cold ethanol to obtain 4.05 g of a whited intended compound (the yield was 90%).

Melting point: 102° to 103° C.
$^1$H-NMR spectrum ($d_6$-DMSO, ppm): 7.84 (1H, s) 8.40 (1H, s).
Mass spectrum (FD): 45 (molecular ion peak).

| | Elementary analysis: | |
|---|---|---|
| | Calculated Values | Found Values |
| C(%) | 26.66 | 26.67 |
| H(%) | 6.72 | 6.57 |
| N(%) | 31.10 | 30.92 |

The structure of this formamidine formate could also be determined by converting the formamidine formate to formamidine picrate, which is a known substance. Namely, 225 mg (2.5 millimoles) of formamidine formate prepared according to the above process was dissolved in 4 ml of ethanol, and 30 ml of an ethanol solution of 572 mg (2.5 millimoles) of picric acid was added dropwise to the above solution. The mixture was stirred at room temperature to precipitate a yellow solid. The solid was recovered by filtration and washed with 5 ml of ethanol to obtain 562 mg of intended formamidine picrate (the yield was 83%).

Melting point: 244° to 247° C. (value disclosed in the reference: 246° to 247° C.).
$^1$H-NMR ($d_6$-DMSO, ppm): 7.88 (1H, s), 8.64 (2H, s).

We claim:
1. A cyanoguanidine derivative represented by the following formula (I):

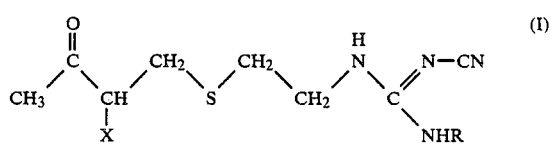

wherein X stands for a hydrogen atom, a chlorine atom or a bromine atom, and R stands for a lower alkyl group.

* * * * *